US011898961B2

United States Patent
Miller et al.

(10) Patent No.: US 11,898,961 B2
(45) Date of Patent: Feb. 13, 2024

(54) SYSTEM AND METHOD FOR DETECTING A PERIPROSTHETIC INFECTION

(71) Applicant: ALIO, Inc., Broomfield, CO (US)

(72) Inventors: Forrest Miller, Philadelphia, PA (US); Samit Kumar Gupta, Menlo Park, CA (US); David John Kuraguntla, Bel Air, MD (US); Elsa Swanson, Cherry Hill, NJ (US)

(73) Assignee: Alio, Inc., San Francisco, CA (US)

( * ) Notice: Subject to any disclaimer, the term of this patent is extended or adjusted under 35 U.S.C. 154(b) by 426 days.

(21) Appl. No.: 16/838,253

(22) Filed: Apr. 2, 2020

(65) Prior Publication Data
US 2020/0232983 A1 Jul. 23, 2020

Related U.S. Application Data

(63) Continuation of application No. PCT/US2018/050675, filed on Sep. 12, 2018.
(Continued)

(51) Int. Cl.
*G01N 33/50* (2006.01)
*G01N 21/51* (2006.01)
(Continued)

(52) U.S. Cl.
CPC ......... *G01N 21/8483* (2013.01); *G01N 21/51* (2013.01); *G01N 33/5094* (2013.01);
(Continued)

(58) Field of Classification Search
CPC ........ G01N 21/8483; G01N 2333/914; G01N 33/558; G01N 2800/102; G01N 33/54386;
(Continued)

(56) References Cited

U.S. PATENT DOCUMENTS

2007/0255357 A1 11/2007 Rose et al.
2008/0050830 A1* 2/2008 Floriano ............ G01N 33/5094
436/63
(Continued)

FOREIGN PATENT DOCUMENTS

EP 2848196 A1 3/2015
WO WO-0021435 A1 4/2000
(Continued)

OTHER PUBLICATIONS

EP18855302.8 European Search Report dated Sep. 9, 2021.
(Continued)

*Primary Examiner* — Rebecca M Fritchman
(74) *Attorney, Agent, or Firm* — Rutan & Tucker, LLP (57) ABSTRACT

A system, device and method for measuring markers for a periprosthetic joint infection in a sample of synovial fluid. A sensor reader device includes a vial receptacle for receiving a vial containing synovial fluid. A light source illuminates the vial and an optical sensor detects light scattered and/or absorbed by white blood cells in the fluid sample. An electrical signal corresponding to the intensity of the light received at the optical sensor is detected. A white blood cell concentration is determined from the electrical signal value. The sensor reader device also includes one or more immunoassay strip receptacles. Immunoassay strips for other marker are inserted into the receptacles. Immunoassay optical sensors detect light generated by the immunoassay reaction on the immunoassay strip to determine the concentration of the marker. In example implementations, the device includes an immunoassay strip reader for leukocyte esterase and c-reactive protein.

21 Claims, 6 Drawing Sheets

Related U.S. Application Data (60) Provisional application No. 62/558,259, filed on Sep. 13, 2017.

(51) Int. Cl.
 G01N 21/84 (2006.01)
 G01N 33/543 (2006.01)

(52) U.S. Cl.
 CPC .............. *G01N 2333/4737* (2013.01); *G01N 2333/914* (2013.01); *G01N 2800/26* (2013.01)

(58) Field of Classification Search
 CPC .............. G01N 21/51; G01N 33/5094; G01N 2333/4737; G01N 2800/26; A61B 10/0045; C12Q 1/6883
 See application file for complete search history.

(56) References Cited

U.S. PATENT DOCUMENTS

| | | | |
|---|---|---|---|
| 2009/0024041 A1 | 1/2009 | Cho et al. | |
| 2009/0215072 A1 | 8/2009 | McDevitt et al. | |
| 2012/0053434 A1 | 3/2012 | Saito | |
| 2014/0011232 A1 | 1/2014 | Vidal et al. | |
| 2015/0011412 A1* | 1/2015 | Deirmengian | G01N 33/5748 435/6.12 |
| 2015/0031049 A1 | 1/2015 | Kentsis et al. | |
| 2015/0157262 A1 | 6/2015 | Schuessler et al. | |
| 2015/0374245 A1 | 12/2015 | Szilagyi | |
| 2016/0112775 A1 | 4/2016 | Kim et al. | |
| 2016/0153878 A1 | 6/2016 | Candon et al. | |
| 2016/0198961 A1 | 7/2016 | Homyk et al. | |
| 2016/0367155 A1 | 12/2016 | Barrett et al. | |
| 2017/0055845 A1 | 3/2017 | Mirov et al. | |
| 2021/0212616 A1 | 7/2021 | Honore et al. | |

FOREIGN PATENT DOCUMENTS

| | | |
|---|---|---|
| WO | WO-2009045374 A2 | 4/2009 |
| WO | WO-2010036930 A1 | 4/2010 |
| WO | WO-2014027293 A2 | 2/2014 |
| WO | WO-2017027643 A1 | 2/2017 |
| WO | WO-2017096138 A1 | 6/2017 |
| WO | WO-2018183558 A1 | 10/2018 |
| WO | WO-2019055520 A1 | 3/2019 |

OTHER PUBLICATIONS

Gille, W. "Chord Length Distributions of the Hemisphere," Journal of Mathematics and Statistics, vol. 1, No. 1, pp. 24-28, 2005.
Kapadia et al., "Periprosthetic joint infection" The Lancet, vol. 387, No. 10016,Jun. 29, 2015 (Jun. 29, 2015), pp. 386-394,XP029394002,ISSN: 0140-6736, DOI:10.1016/S0140-6736(14)61798-0.
Steuer et al., "Noninvasive transcutaneous determination of access blood flow rate," Kidney International, vol. 60, pp. 284-291, 2001.
U.S. Appl. No. 16/082,249 Notice of Allowance dated May 26, 2021.
EP18775541.8 European Search Report dated Dec. 9, 2020.
U.S. Appl. No. 16/082,249 Notice of Allowance dated Dec. 30, 2020.
U.S. Appl. No. 16/082,249 Office Action dated Oct. 14, 2020.
Co-pending U.S. Appl. No. 16/082,249, filed Sep. 4, 2018.
PCT/US2018/024925 International Search Report dated Jul. 26, 2018. 5 Pages.
PCT/US2018/024925 Written Opinion dated Jul. 26, 2018. 11 Pages.
PCT/US2018/050675 Search Report dated Nov. 21, 2018.
Schmitt, J. M., Simple photon diffusion analysis of the effects of multiple scattering on pulse oximetry. IEEE Transactions on Biomedical Engineering, vol. 38, No. 12, pp. 1194-1203, 1991.
Schweiger et al. The finite element method for the propagation of light in scattering media: boundary and source conditions. Medical Physics, vol. 22, No. 11, pp. 1779-1792, 1995.
EP18775541.8 European Search Report dated Apr. 1, 2021.
U.S. Appl. No. 16/082,249 Notice of Allowance dated Apr. 26, 2021.

* cited by examiner

SYSTEM AND METHOD FOR DETECTING A PERIPROSTHETIC INFECTION

CROSS-REFERENCE TO RELATED APPLICATIONS

This application is a continuation of PCT Application No. PCT/US2018/050675, filed Sep. 12, 2018, which claims the benefit of U.S. Provisional Application No. 62/558,259, filed Sep. 13, 2017, which applications are incorporated herein by reference.

BACKGROUND

The present disclosure relates to diagnostic methods and systems for detecting and measuring markers for infections, and more particularly to systems and methods for detecting periprosthetic joint infections.

Total joint arthroplasty (TJA) is one of the most commonly performed procedures in the United States. More than 1.4 million primary procedures and 130,000 revisions were performed in 2015, with volumes expected to double in the upcoming decade. Periprosthetic joint infection (PJI) is a condition in an implant caused by bacteria colonizing the implant. PJI is one of the primary causes of premature implant failure, accounting for 25.2% of all revision surgeries. At a cost of over $110,000 per revision, periprosthetic joint infection costs the American healthcare system over $3.5 billion each year.

Until 2018, the Musculoskeletal Infection Society (MSIS) defined the following diagnostic criteria for PJI:
1. A sinus tract communicating with the prosthesis is present in the implant; or
2. A pathogen is isolated by culture from at least two separate tissue or fluid samples obtained from the affected prosthetic joint; or
3. Four of the following six criteria exist:
   a. Elevated serum erythrocyte sedimentation rate (ESR) and serum C-reactive protein (CRP) concentration,
   b. Elevated synovial leukocyte count,
   c. Elevated synovial neutrophil percentage (PMN %),
   d. Presence of purulence in the affected joint,
   e. Isolation of a microorganism in one culture of periprosthetic tissue or fluid, or
   f. Greater than five neutrophils per high-power field in five high-power fields observed from histologic analysis of periprosthetic tissue at ×400 magnification.

The MSIS now defines the following preoperative criteria, with an associated scoring system, for the diagnosis of PJI:
  2 positive bacterial cultures—6 points
  Presence of a sinus tract—6 points
  Synovial fluid WBC count >3000 cells/µL—3 points
  Presence of alpha-defensin in synovial fluid—3 points
  Presence of leukocyte esterase (++ per immunoassay strip) in synovial fluid—3 points
  PMN %>80% —2 points
  Serum CRP>1 mg/dL—2 points
  Serum D-dimer >860 ng/mL—2 points
  Serum ESR>30 mm/h—1 point
  Synovial fluid CRP>6.9 mg/L—1 point
A combined score of greater than or equal to 6 indicates an infected patient. A combined score between 2 and 5 requires intraoperative results to confirm or refute the diagnosis of PJI. A combined score of 1 or 0 indicates an uninfected patient.

The current clinical algorithm for the diagnosis and treatment of PJI involves a multidisciplinary test battery administered to patients who present with one or more of a range of symptoms including pain, fever, warmness, and purulent secretions or fistulae at the surgical site or elsewhere. A symptomatic patient will undergo a stepwise diagnostic battery beginning with blood tests for systemic markers of inflammation, which are by definition non-specific to PJI.

Imaging tests will usually be performed to augment this serum analysis. These tests, which include multiple-angle x-rays and radioisotope imaging, are intended to identify bone loss and implant loosening. These are non-specific markers for infection: the presence of either indicates a problem but does not identify the cause, and the absence of both does not rule out an infection.

If, after administering the above tests, the clinician suspects an infection, an arthrocentesis may be performed, whereby synovial fluid is aspirated from the joint with a needle. This sample is used to obtain both a total cell count and differential leukocyte count. The total cell count determines the total concentration of cells, including white blood cells (WBCs), present in the fluid. The differential leukocyte count is a more granular test that evaluates the relative concentrations of different types of white blood cells. If the WBC concentration is high (>10,000-30,000/µL), and mostly made up of neutrophils (>64-78%), an infection is likely. In addition, the fluid sample may be cultured for both aerobic and anaerobic bacteria. These cultures have relatively high rates of false negatives, but are still considered the gold standard for diagnosing PJI due to the deficiencies of the other available tests.

The fluid sample may then be sent off to a third-party laboratory for further testing by immunoassays for synovial fluid biomarkers: proteins that are innately released in high numbers in response to infection. These tests, particularly for the peptide alpha-defensin and the enzyme leukocyte esterase (LE), exhibit low rates of false negatives and false positives compared to the current diagnostic standard.

The problem with these tests is they are not performed at the point-of-care. Samples must instead be shipped to a specialized laboratory for analysis. The WBC counts and the differential leukocyte count are performed in a laboratory using a microscope. The cultures must be grown in a lab and monitored over a period of time that may last days.

It would be advantageous to be able to perform the analysis of the criteria for PJI at the patient's point-of-care, such as a doctor's office, hospital clinic, or interventional radiology suite. It would also be advantageous to be able to obtain results at the point-of-care with a lower rate of false negatives and false positives.

SUMMARY

In view of the above, devices, systems and methods are provided to analyze criteria for PJI at the patient's point-of-care.

In an aspect, a system for detecting an infection in a fluid sample drawn from a patient at the patient's point-of-care is provided. The system may include a white blood cell ("WBC") concentration function configured to determine a WBC concentration from the fluid sample. The WBC concentration function may comprise a vial receptacle for receiving a vial containing the fluid sample, one or more light sources configured to illuminate the fluid sample in the vial, and one or more vial optical sensors configured to detect scattered and/or absorbed light intensity by white blood cells in the fluid sample and to convert this light intensity to a vial electrical signal. The system may comprise at least one immunoassay (IA) strip function configured to determine a marker concentration of a selected marker in the fluid sample. The IA strip function may comprise at least one IA strip receptacle configured to receive an IA strip having a marker reagent and a portion of the fluid sample. The marker reagent may be configured to generate at least one marker light intensity from a reaction between the marker reagent and a marker in the fluid sample. The IA strip function may comprise an IA strip optical sensor configured to detect the marker light intensities and to convert the marker light intensities to IA marker electrical signals. The system may comprise an optical sensor reader configured to receive the vial electrical signal and the IA marker electrical signal(s), and to store the vial electrical signal as vial sensor data and the IA marker electrical signal(s) as IA marker sensor data. The system may comprise a communications interface, which communicates the vial sensor data and the IA marker sensor data to a sensor data processor configured to determine a WBC concentration and a polymorphonuclear percentage from the vial sensor data and from the IA marker sensor data.

Optionally, in any embodiment, the marker is leukocyte esterase (LE), the marker reagent is a LE reagent, and the IA strip marker optical sensor is a LE optical sensor configured to detect the marker light intensity at a wavelength range specific to the LE marker-reagent reaction. Optionally, in any embodiment, the selected wavelength range is 425-475 nm. Optionally, in any embodiment, the system further comprises: a CRP immunoassay strip receptacle configured to receive a CRP immunoassay strip having a portion of the fluid sample and a CRP reagent configured to react with CRP in the fluid sample. Optionally, in any embodiment, the system further comprises a CRP optical sensor configured to detect light generated by the reaction of CRP with the CRP reagent. Optionally, in any embodiment, the system further comprises a quality control optical sensor configured to detect light generated by the LE immunoassay strip, wherein the selected wavelength range is 600-630 nm corresponding to a detected wavelength for light reflected by hemoglobin in the fluid sample. Optionally, in any embodiment, the marker is alpha-defensin, the marker reagent is an alpha-defensin reagent, and the IA strip marker optical sensor is an alpha-defensin optical sensor configured to detect the marker light intensity at a wavelength range specific to the alpha-defensin marker-reagent reaction. Optionally, in any embodiment, the selected wavelength range is 400-700 nm.

In another aspect, a system for detecting an infection in synovial fluid drawn from a patient is provided. The system may comprise a vial receptacle for holding a vial containing a fluid sample. The system may comprise a light source disposed in the vial receptacle to illuminate the fluid sample in the vial. The system may comprise a vial optical sensor disposed in the vial receptacle to detect light scattered by white blood cells in the fluid sample and to generate a vial electrical signal indicative of an intensity of the light detected. The system may comprise at least one immunoassay strip receptacle for holding a corresponding at least one immunoassay strip, wherein each at least one immunoassay strip includes a reagent configured to react with a corresponding at least one marker substance and to generate light substantially within a wavelength range corresponding to the marker substance when the immunoassay strip is in contact with the fluid sample. The system may comprise at least one optical sensor in each of the at least one immunoassay strip receptacle, each optical sensor corresponding to one of the at least one marker substance and configured to detect light within the wavelength range corresponding to the one of the at least one marker substance when the at least one immunoassay strip is inserted into the at least one immunoassay strip receptacle, wherein the at least one optical sensor generates an immunoassay electrical signal indicative of the intensity of light detected within the wavelength range corresponding to the one of the at least one marker substance. The system may comprise a communications interface configured to receive the vial electrical signal, the first immunoassay electrical signal, and the second immunoassay electrical signal as sensor data, and to communicate the sensor data to a sensor data processor configured to analyze the sensor data to diagnose the presence or absence of a periprosthetic joint infection in the fluid sample.

Optionally, in any embodiment, the at least one marker substance includes leukocyte esterase (LE) and c-reactive protein (CRP). Optionally, in any embodiment, the at least one immunoassay strip receptacle includes: a LE immunoassay strip receptacle configured to receive a LE immunoassay strip having a LE reagent configured to react with LE; and a CRP immunoassay strip receptacle configured to receive a CRP immunoassay strip having a CRP reagent configured to react with CRP. Optionally, in any embodiment, the at least one sensor includes: a LE optical sensor configured to detect light generated by the reaction of LE with the LE reagent, wherein the selected wavelength range is 425-475 nm. Optionally, in any embodiment, the at least one sensor includes a CRP optical sensor configured to detect light generated by the reaction of CRP with the CRP reagent. Optionally, in any embodiment, the at least one sensor includes a quality control optical sensor configured to detect light generated by the LE immunoassay strip, wherein the selected wavelength range is 600-630 nm corresponding to a detected wavelength for light reflected by hemoglobin in the fluid sample.

In another aspect, a method for evaluating markers for periprosthetic joint infection (PJI) in a synovial fluid sample is provided. The method may comprise detecting the presence of a vial containing fluid sample in a vial receptacle. The method may comprise applying power to a light source directed at the vial containing fluid sample. The method may comprise initiating a vial optical sensor. The method may comprise inputting vial electrical signals representing a vial light intensity received from the vial optical sensor for a time period T1, wherein the vial light intensity is a composite measurement derived from light from the light source reflected and absorbed by white blood cells in the fluid sample. The method may comprise storing the vial electrical signals as vial sensor data. The method may comprise detecting the presence of a leukocyte esterase (LE) immunoassay (IA) strip in a LE IA receptacle, wherein the LE IA strip includes a LE reagent and a portion of the fluid sample. The method may comprise initiating a LE optical sensor. The method may comprise inputting LE IA electrical signals representing light detected by the LE IA optical sensor, wherein the light detected by the LE optical sensor is generated by a reaction between the LE reagent and leukocyte esterase in the fluid sample. The method may comprise storing the LE IA electrical signals as LE sensor data. The method may comprise communicating the vial sensor data and the LE sensor data to a sensor data processor to determine a white blood cell concentration (WBC) from the vial sensor data and a leukocyte concentration from the LE sensor data.

Optionally, in any embodiment, the step of inputting LE IA electrical signals includes detecting the light at a wavelength range of 425-475 nm as a ratio to the amount of detected light at a wavelength range of 500-550 nm. Optionally, in any embodiment, the method further comprises detecting the presence of a c-reactive protein (CRP) immunoassay (IA) strip in a CRP IA receptacle, wherein the CRP IA strip includes a CRP reagent and a portion of the fluid sample. Optionally, in any embodiment, the method further comprises initiating a CRP optical sensor. Optionally, in any embodiment, the method further comprises inputting CRP IA electrical signals representing light detected by the CRP optical sensor, wherein the light detected by the CRP optical sensor is generated by a reaction between the CRP reagent and c-reactive protein in the fluid sample. Optionally, in any embodiment, the method further comprises storing the CRP IA electrical signals as CRP sensor data. Optionally, in any embodiment, the method further comprises communicating the CRP sensor data to the sensor data processor to determine a CRP concentration from the CRP sensor data.

Optionally, in any embodiment, the method further comprises initiating a hemoglobin (Hb) optical sensor. Optionally, in any embodiment, the method further comprises inputting Hb electrical signals representing light detected by the Hb optical sensor, wherein the light detected by the Hb optical sensor is light reflected by hemoglobin in the fluid sample. Optionally, in any embodiment, the method further comprises storing the Hb electrical signals as Hb sensor data. Optionally, in any embodiment, the method further comprises communicating the Hb sensor data to the sensor data processor to use as a quality control parameter in analyzing the LE sensor data. Optionally, in any embodiment, the step of inputting Hb electrical signals includes detecting the light at a wavelength range of 600-630 nm. Optionally, in any embodiment, the method further comprises determining a neutrophil percentage (PMN) as the LE concentration divided by the WBC concentration and multiplying by 100%.

In another aspect, a system for measuring markers for an infection in synovial fluid drawn from a patient is provided. The system may comprise a vial receptacle for holding a vial containing a fluid sample. The system may comprise a light source disposed in the vial receptacle to illuminate the fluid sample in the vial. The system may comprise a vial optical sensor disposed in the vial receptacle to detect light scattered by white blood cells in the fluid sample and to generate a vial electrical signal indicative of an intensity of the light detected. The system may comprise a first immunoassay strip receptacle for holding a first immunoassay strip having a first reagent configured to react with a first substance as a marker for a periprosthetic infection and to generate light substantially within a first wavelength range when the first immunoassay strip is in contact with the fluid sample. The system may comprise a first optical sensor configured to detect light in the first wavelength range when the first immunoassay strip is inserted into the first immunoassay strip receptacle and to generate a first immunoassay electrical signal indicative of the intensity of light detected within the first wavelength range. The system may comprise a second immunoassay strip receptacle for holding a second immunoassay strip having a second reagent configured to react with a second substance as another marker for a periprosthetic infection and to generate light substantially within a second wavelength range when the second immunoassay strip is in contact with the fluid sample. The system may comprise a second optical sensor configured to detect light in the second wavelength range when the second immunoassay strip is inserted into the second immunoassay strip receptacle and to generate a second immunoassay electrical signal indicative of the intensity of light detected within the second wavelength range. The system may comprise a communications interface configured to receive the vial electrical signal, the first immunoassay electrical signal, and the second immunoassay electrical signal as sensor data, and to communicate the sensor data to a sensor data processor configured to analyze the sensor data to diagnose the presence or absence of a periprosthetic joint infection in the fluid sample.

In another aspect, a method for evaluating markers for periprosthetic joint infection (PJI) in a synovial fluid sample is provided. The method may comprise detecting the presence of a vial containing fluid sample in a vial receptacle. The method may comprise applying power to one or more light sources directed at the vial containing fluid sample. At least one vial optical sensor may be activated to read a light intensity from the vial. Vial electrical signals representing a vial light intensity may be received from each vial optical sensor for a time period T1. Optionally, in any embodiment, vial light intensity may be light from the light source reflected off white blood cells in the fluid sample. Optionally, in any embodiment, vial light intensity is light that has passed through, rather than been absorbed by, white blood cells in the fluid sample. The vial electrical signals may be stored as vial sensor data. The presence of a leukocyte esterase (LE) immunoassay (IA) strip may be detected in a LE IA receptacle. The LE IA strip may comprise a LE reagent and a portion of the fluid sample. A LE optical sensor may be initiated for reading light intensity from the LE IA strip. LE IA electrical signals representing light detected by the LE IA optical sensor may be received during reading of the light intensity from the LE IA optical sensor. The light detected by the LE optical sensor may be generated by a reaction between the LE reagent and leukocyte esterase in the fluid sample. In addition to directly measuring light generated by immune binding reactions, the LE optical sensor may detect reflected light that originated in a light source integrated with the sensor. This light measured by the sensor may be of the same wavelength as the light source, termed reflectance, or a different wavelength, termed fluorescence. The LE IA electrical signals may be stored as LE sensor data. The vial sensor data and the LE sensor data may be communicated to a sensor data processor to determine a white blood cell concentration (WBC) from the vial sensor data and a PMN % from the LE sensor data. The LE sensor data is analyzed to determine the concentration of the enzyme in the fluid sample. This data may be further analyzed to produce a binary result indicating the presence of LE either above or below a certain threshold. The WBC concentration, LE concentration, and the PMN % may be reported for use in determining whether the patient has a PJI.

Some examples of devices, systems, and methods for detecting an infection in a fluid sample drawn from a patient at the patient's point-of-care are outlined above rather broadly in order that the detailed description thereof may be better understood, and in order that the present contribution to the art may be better appreciated. Additional example implementations of the devices, systems, and methods are described below and will form the subject matter of the claims appended hereto. In this respect, before explaining at least one example of the devices, systems, and methods in detail, it is to be understood that the devices, systems, and methods are not limited in their application to the details of construction or to the arrangements of the components set forth in the following description or illustrated in the drawings. Other example implementations of the devices, systems, and methods may be developed, practiced and carried out in various ways. Also, it is to be understood that the phraseology and terminology employed herein are for the purpose of the description and should not be regarded as limiting.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION

I. System Description

Disclosed herein are systems and methods that use multimodal sensor devices for detecting evaluating markers used to determine the presence of an infection in synovial fluid drawn from a patient. The multimodal sensor device proposed here provides diagnostic information at the point of care, indicating to the clinician what follow-on actions are appropriate.

An example implementation of the sensor reader device is a point-of-care, multimodal sensor platform that identifies the presence and/or measures the concentrations of several established biomarkers for infection in an aspirated synovial fluid sample. Potential markers include: white blood cell (WBC) concentration, leukocyte esterase (LE), C-reactive protein (CRP), alpha-defensin and hemoglobin. From these direct measurements, the device may also be configured to determine the polymorphonuclear cell (PMN) percentage and presence of lysed red blood cells in the fluid. Each of these markers, and the sensor modality for its detection, is described below.

A. WBC Concentration:

The WBC concentration is a measure of the total white cell count in the synovial fluid. The WBC concentration is one of the MSIS criteria with a comparatively high diagnostic score of 3 (see Background) and a widely accepted marker for infections in general. In an example implementation, the sensor reader device includes an optical sensor that quantifies the WBC concentration in synovial fluid. An example implementation of a WBC optical sensor is described in more detail below with reference to FIGS. 1 and 4.

B. Leukocyte Esterase

Leukocyte esterase (LE) is an enzyme released by neutrophils, which are specialized leukocytes (white blood cells) recruited to a surgical site to fight a developing bacterial infection. LE is also one of the MSIS criteria with a diagnostic score of 3, and has shown strong predictive power and high correlations with multiple MSIS criteria—including WBC count, PMN percentage and CRP level. This makes a LE assay a strong confirmatory test for PJI. The LE assay may be implemented using lateral flow or dipstick-like immunoassay strips, which may be configured to exhibit a colorimetric reaction in the presence of the LE enzyme. The colorimetric reaction is measurable using an optical sensor as described in more detail below with reference to FIGS. 1 and 2B.

C. C-Reactive Protein

C-reactive protein (CRP) is a substance produced by the liver in elevated concentrations in the presence of inflammation. CRP may be measured in the serum, but has improved diagnostic specificity in the synovial fluid. While it is a general inflammatory marker, rather than a specific indicator of infection, CRP level is one of the MSIS criteria and therefore provides the sensor reader device enhanced diagnostic power. As with LE, CRP may be measured semi-quantitatively using a rapid immunoassay and optical measurement techniques in concert. A CRP immunoassay strip, receptacle, and a CRP optical sensor are described in more detail below with reference to FIGS. 1 and 2B.

D. Alpha Defensin

Alpha defensin is a small peptide released by white blood cells, particularly neutrophils, for the purpose of fighting various types of infection. Alpha defensin is particularly active in the body's response to bacteria, both Gram-positive and Gram-negative. Alpha defensin, along with WBC count and LE, has an MSIS diagnostic score of 3, making it a predictive marker for PJI.

E. Neutrophil (PMN) Percentage

The PMN may be determined by differential analysis of the total WBC concentration in the fluid sample. The PMN percentage indicates the relative abundance of the specific type of white cell that fights bacterial infection. The PMN measure increases sharply in the presence of PJI and may be indirectly calculated to a useful degree of accuracy from a quantitative or semi-quantitative leukocyte esterase test. The PMN percentage may be derived computationally from the combined outputs of the WBC and LE sensors to yield the metric outlined in the MSIS criteria as described below with reference to FIG. 3.

F. Hemoglobin

Hemoglobin is an indicator of the presence of red blood cells in the fluid sample. Because the device uses optical sensing modalities, significant amounts of blood may affect the output and diagnostic power of the sensor measurements. The hemoglobin measurement may be used to calibrate the sensor output and/or invalidate the results to reduce false negatives. A dual wavelength detection scheme may be used in an example implementation of the sensor reader device. The optical sensing modality that measures the leukocyte esterase (LE) concentration in the fluid sample can be straightforwardly modified to quantify the amount of hemoglobin, and therefore blood, in the sample. An additional photodetector, tuned to the wavelength of light reflected by hemoglobin (600-650 nm), may be incorporated into the LE sensor. The hemoglobin metric may be used in the measurement processing for cellular and LE concentration by providing a quantitative correction factor for the amount of blood present in a fluid sample.

G. System for Measuring Markers for PJI

The sensor reader device may be configured to communicate electrical signals indicative of the white blood cell concentration, LE concentration, CRP concentration and any other measured metrics to a sensor data processor to quantify the results (including the calculation of the PMN) and to generate a meaningfully formatted report. The sensor data processor may be provided within the sensor reader device, in a hub wirelessly connected to the device, or in a cloud server connected to the sensor reader device over a data network.

The sensor reader device may be configured as a benchtop device and equipped for use at a point-of-care location, such as, for example, a physician's office or other care site that may not have adequate access to a diagnostic laboratory. The device may have network access to a database, which may be implemented using a cloud service. The results of the measurements taken by the sensor reader device may be stored in patient records in the database accessible over the Internet and available to the patient's physician anywhere and at any time. A physician may access the results from a web-based portal or an electronic health record (EHR). The sensor reader device may have a display which displays the test results.

The integration of multiple sensors for multiple markers included in the MSIS diagnostic criteria in the sensor reader device provides levels of diagnostic accuracy comparable to the current gold standard at the clinical point of care.

II. Sensor Reader Device

Figure 1:
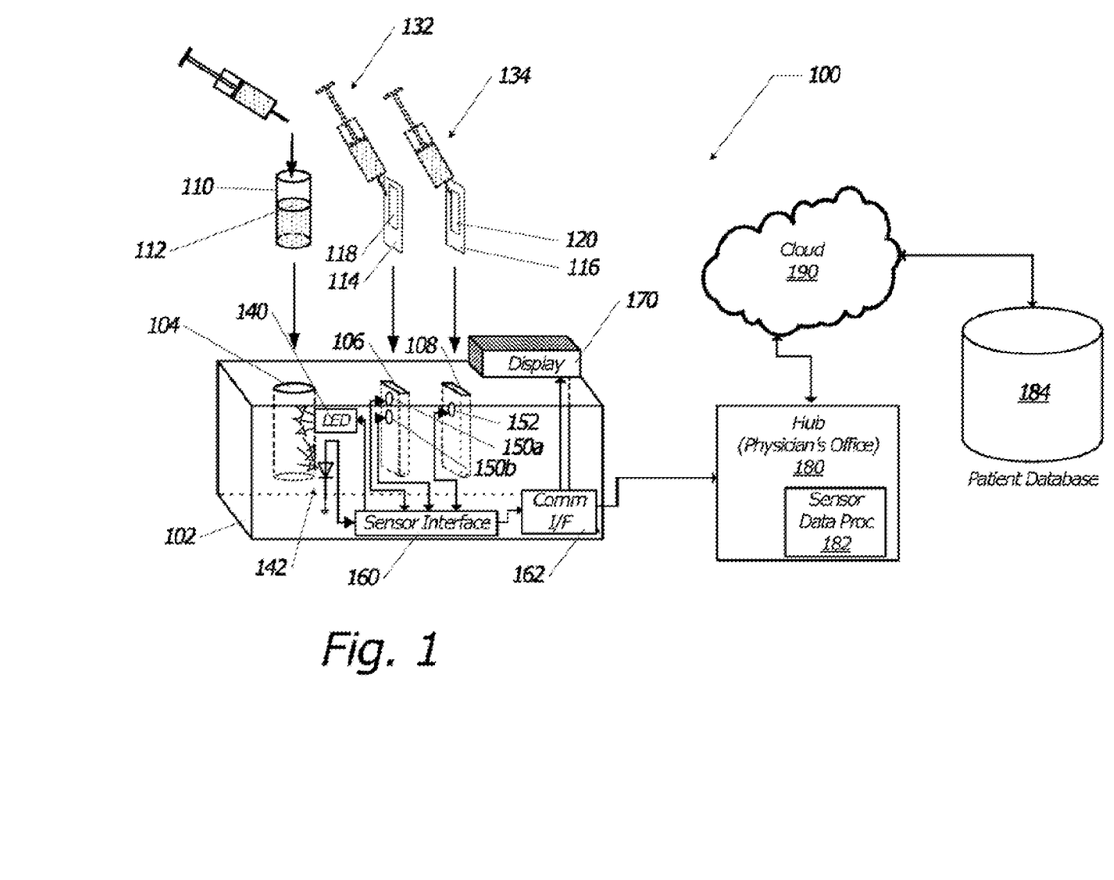
FIG. 1 is a schematic diagram of an example implementation of a system for detecting an infection in a fluid sample drawn from a patient at the patient's point-of-care.

FIG. 1 is a schematic diagram of an example implementation of a system 100 for detecting an infection in a fluid sample 112 drawn from a patient at the point-of-care. The system 100 includes a sensor reader device 102 connected over a data network to a data processing hub (hub) 180. The hub 180 may be a subcomponent housed within the device 102, rather than a separate piece of hardware. The sensor reader device 102 obtains sensor readings for obtaining a white blood cell (WBC) concentration, a leukocyte esterase (LE) concentration, a c-reactive protein (CRP) concentration, and a hemoglobin concentration or other representative metric for the blood content of the sample. The sensor reader device 102 includes a communication interface 162 for connecting over a data network to the hub 180. The sensor reader device 102 communicates sensor data to the hub 180. The hub 180 may be connected to a cloud service 190 over the Internet. The cloud service 190 may provide data storage services in a database 184. A periprosthetic joint infection (PJI) data processing system to process the sensor data and obtain meaningful results that may allow a physician to diagnose a PJI may reside in the device 102, the hub 180 or the cloud service 190. The hub 180 may be configured to communicate PJI test results to the database 184 for storage with the patient's records. The patient's records may be made accessible to the physician via a web-based portal or an electronic health record (EHR). It is noted that the use of a cloud-based service is optional. A service may be implemented using a simple website, or other service infrastructure.

The sensor reader device 102 in FIG. 1 includes a vial receptacle 104, a LE immunoassay strip receptacle 106, and a CRP immunoassay strip receptacle 108. The vial receptacle 104 may be configured to receive a vial 110 containing a fluid sample 112. The term vial as used throughout this disclosure is intended to encompass any container used to contain the sample during analysis including but not limited to a vial, a cartridge, cuvette, capillary tube, microfluidic device or the like. The LE immunoassay strip receptacle 106 may be configured to receive a LE immunoassay strip 114, and the CRP immunoassay strip receptacle 106 may be configured to receive a CRP immunoassay strip 116. The vial receptacle 104, the LE immunoassay strip receptacle 106, and the CRP immunoassay strip receptacle 108 may be configured to prevent ambient light from entering each receptacle. In an example implementation, the vial receptacle 104 may be the exact height of the transparent sample tube (i.e. vial 110), the top of which may not be optically transparent, so to prevent ambient light from entering the vial receptacle 104. The immunoassay strip receptacles 106, 108 may be equipped with either a spring-loaded door, such that inserting an immunoassay strip will automatically shut the assay chamber. Alternatively, test strips may be placed into a sliding drawer or cartridge, which will block out ambient light when placed into the device for analysis.

Prior to the taking of measurements on the sensor reader device 102, a healthcare professional—such as an orthopedic surgeon, interventional radiologist, nurse or technician—may perform an arthrocentesis, which involves using a syringe 130 to aspirate synovial fluid from the patient's knee. The aspirated synovial fluid may be transferred into the vial 110, which may be a standard fluid collection tube of diameter 13 mm and height 75 mm. These tubes may be commonly referred to by the brand name Vacutainer™. The particular type of tube most commonly used to collect synovial fluid post-arthrocentesis includes the anticoagulant ethylenediaminetetraacetic acid (EDTA). These tubes may be made of glass, but may be more commonly made from polystyrene or polyethylene terephthalate (PET), which approximate the optical properties of a glass tube. It is noted that in other example implementations, the system may be tuned to operate using other sized fluid collection tubes.

From the aspirating syringe, a first drop of the fluid sample on the order of 10-100 microliters (µl) may be disposed on a LE immunoassay 118 at 132. The LE immunoassay 118 contains a LE reagent configured to react with the LE that may be contained in the fluid sample. A second drop of the fluid sample, also on the order of µL's, may be disposed on a CRP immunoassay 120 at 134. The CRP immunoassay 120 contains a CRP reagent configured to react with the CRP that may be contained in the fluid sample.

After preparing the LE immunoassay strip 114 and the CRP immunoassay strip 116, the technician inserts the vial 110 containing the fluid sample 112 into the vial receptacle 104. The vial receptacle 104 may include a switch (described in more detail with reference to FIG. 4) that may be triggered by insertion of the vial 110 to power 'on' or to start an initialization procedure for a WBC concentration measurement. The sensor reader device 102 includes one or more WBC light sources 140 positioned in the vial receptacle 104 so as to illuminate a vial that has been inserted into the vial receptacle 104. The sensor reader device 102 also includes one or more WBC optical sensors 142 positioned in the vial receptacle 104 so as to receive light scattered or absorbed by white blood cells in the fluid sample 112 when the vial 110 in the vial receptacle 104 may be illuminated by the WBC light source 140.

The WBC light source 140 may be any suitable electrically powered light source. In an example implementation, the WBC light source 140 may be a light-emitting diode (LED). The WBC optical sensor 142 may be a photodiode.

In an example implementation, the WBC light source 140 and the WBC optical sensor 142 may be implemented as an LED and photodiode, respectively, that may be precisely tuned and selected for sensitivity to a wavelength range (such as, for example, ~580-595 nm) of wavelengths centered, for example, at 587 nm, which has been determined to be the peak wavelength at which light may be scattered by leukocytes in synovial fluid.

The WBC optical sensor(s) 142 may be positioned in an optimal position for receiving light scattered by the white blood cells. In an example implementation, the WBC optical sensor 142 may be positioned 90° from the WBC light source 140 about an axis through the center of the vial 110 when in the vial receptacle 104. Multiple optical sensors 142 may be placed at relative angles ranging from 0° to 180° around the vial 110.

During the reading of the WBC optical sensor 142, light scattered by the leukocytes present in the fluid sample will induce a voltage in the WBC optical sensor 142, which may be a photodiode operating in photovoltaic mode. In this mode, the photodiode voltage generates an electrical signal, such as a voltage level indicative of the light intensity of the scattered light received by the photodiode. The voltage, which may be amplified using a transimpedance amplifier as described below with reference to FIG. 4, may be correlated with the leukocyte concentration in the synovial fluid and serves as a WBC electrical signal, the output parameter of the device 102.

In operation, the vial 110 may be inserted in the vial receptacle 104, which may trigger a switch to either turn the power to the device 102 on, or to initialize the system, or to initiate a reading of the vial optical sensor 140. The sensor reader device 102 includes a display 170, which may be used to display a status message indicating the status of the device 102. For example, placing the vial 110 in the device 102 activates the device 102 to take a white blood cell count measurement, which may be indicated as "in progress" on the display 170. The display 170 may also indicate by display of a message that the measurement is complete. In example implementations, the sensor reading of the WBC optical sensor 142 may take approximately 10-120 seconds. When the display 170 indicates the reading is complete and optionally displays the results of the assay, the vial 110 may be removed and prepared for further analysis, if appropriate.

The WBC electrical signal, which may be the sensor output, may be communicated via a sensor interface 160 to the communications interface 162 (which may be hardwired—and use analog communication or a digital communication protocol such as Inter-Integrated Circuit (I²C) or Serial Peripheral Interface (SPI)—or may use a wireless communication protocol such as Bluetooth or the like) to be transmitted to a company database, for example, or the patient's EHR. The WBC electrical signal may be analyzed to produce an accurate and WBC count, which may then be displayed on the display 170 on the device 102. The analysis of the WBC electrical signal may be performed using a sensor data processor 182 operating in the cloud 190 in the example in FIG. 1. In some example implementations, the sensor data processor 182 may be implemented as a component of the sensor reader device 102.

To obtain the LE concentration, and/or a binary representation of the LE concentration above or below a certain threshold, the technician inserts the LE immunoassay strip 114 into the LE immunoassay strip receptacle 106. The LE immunoassay strip receptacle 106 includes a LE optical sensor 150a disposed in the receptacle 106 to receive light generated by the reaction of the fluid sample and the LE reagent on the LE immunoassay 118. The LE measurement uses the LE optical sensor 150a, which may be implemented using one or more photodiode precisely tuned and selected for sensitivity to ranges of a selected wavelength released by the immune binding reactions on the immunoassay strips. In an example implementation, the selected wavelength is 425-475 nm. In another implementation, three wavelength ranges may be analyzed, corresponding to red, green and blue light: 600-630 nm, 500-550 nm and 425-475 nm, respectively. As with the WBC optical sensor 140, the LE photodiode 150a may be operating in photovoltaic mode and the LE electrical signals (e.g. voltages) generated will be transmitted either wirelessly or on a hardwired connection to the database 184 and the patient's EHR.

The LE immunoassay strip receptacle 106 may also include a hemoglobin optical sensor 150b disposed within the receptacle 106. The hemoglobin optical sensor 150b may be a photodetector tuned to the wavelength of light reflected by hemoglobin (i.e. 600-630 nm). The hemoglobin optical sensor 150b may be incorporated into the same package as the LE photodiode 150a. The metric provided by the hemoglobin optical sensor 150b may be incorporated into the measurement algorithms for the WBC concentration and the LE concentration.

To obtain the CRP concentration, and/or a binary representation of the CRP concentration above or below a certain threshold, the technician inserts the CRP immunoassay strip 116 into the CRP immunoassay strip receptacle 108. The CRP immunoassay strip receptacle 108 includes a CRP optical sensor 152 disposed in the receptacle 108 to receive light generated by the reaction of the fluid sample and the CRP reagent on the CRP immunoassay 120. The CRP measurement uses the CRP optical sensor 152, which may be implemented using one or more photodiodes precisely tuned and selected for sensitivity to ranges of a selected wavelength released by the immune binding reactions on the immunoassay strips. As with the WBC optical sensor 140 and the LE optical sensor 150a, the CRP photodiode 152 may be operating in photovoltaic mode and the CRP electrical signals (e.g. voltages) generated will be transmitted either wirelessly or on a hardwired connection to the database 184 and the patient's EHR.

The WBC optical sensor 142, the LE optical sensor 150a, the hemoglobin optical sensor 150b, and the CRP optical sensor 152 may be connected to a sensor interface 160, which includes hardware and, where provided, software, used to process the electrical signals received from the sensors. The sensor interface 160 may simply be a bus or interconnections communicating the sensor electrical signals to the communication interface 162. In some implementations, the sensor interface 160 may include an analog-to-digital converter, digital signal processing functions, and any other function selected for specific implementations.

The communications interface 162 may include any suitable hardware and, where provided, software for processing the sensor electrical signals for communication on a data network. The communications interface 162 may for example implement a wireless communication protocol, such as for example, the Bluetooth LE™ communications protocol. The wireless communications protocol may be any suitable protocol for wireless communications, such as WiFi®, cellular data, or a near-field communication protocol. In some implementations, the communications interface 162 may be for a hardwired connection.

It is noted that the illustrated examples perform measurements for WBC concentration, LE concentration, and CRP concentration for the purpose of detecting RR The methods and example implementations described herein may also be modified or adapted for measuring other markers. A sensor reader device similar to the device 102 may be provided having more or a single immunoassay strip receptacle. Receptacles and accompanying optical sensors may be added for additional assays, or a single receptacle and a single sensor array may be configured for reading multiple selected markers.

For example, in order to detect LE or CRP in an aspirated fluid sample, a small amount of fluid may be added to a lateral flow assay strip with a colorimetric reaction output. The strip, whether purchased off the shelf or produced in a "lab-on-a-chip" or other format specifically for this application, may be placed into the device 102 for analysis of the chromatic output. An optical sensor similar to that used in the WBC measurement modality may be tuned to the specific wavelength of light released by the immunological binding reaction associated with a particular alternative analyte. Rather than measuring the physical scattering of photons from a static source, however, the detector may directly measure the amount of light produced by a chemical reaction. Specifically, monoclonal or polyclonal antibodies specific to an antigen present on the target protein, compound or organism may release photons as a result of binding to their target. This type of colorimetric optical sensor may be modified to account for a variety of light wavelengths, and potentially use one photodiode array to measure a number of markers. A multivalent sensing array may save space, lower costs, potentially reduce time-to-result, and may make integrated measurements, such as for hemoglobin content in the fluid sample, easier to derive.

A. Method for Measuring a WBC Concentration

Figure 2A:
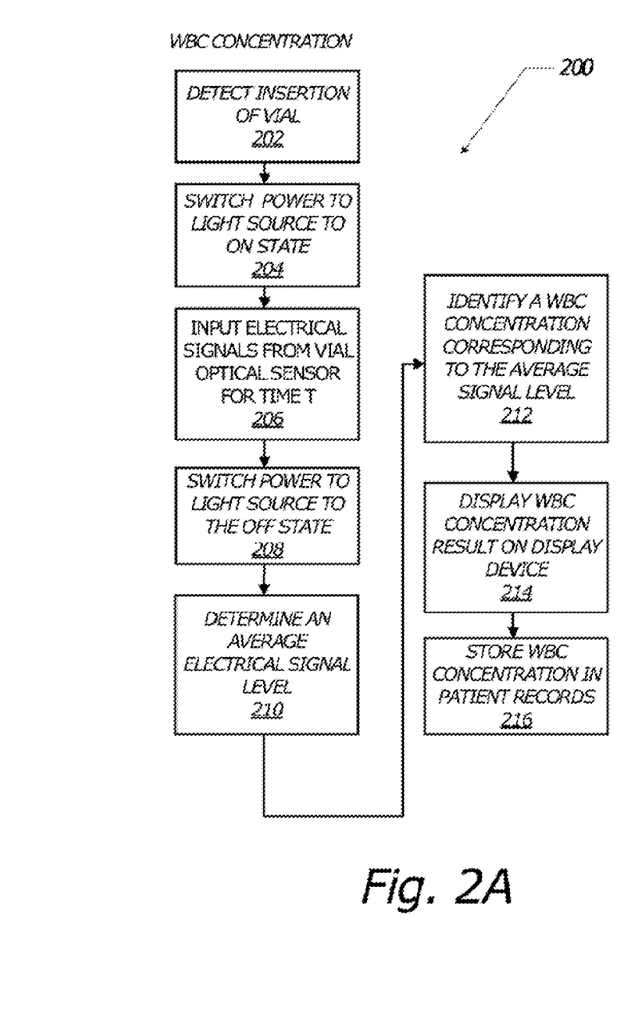
FIG. 2A is a flowchart illustrating operation of an example method of determining a white blood cell concentration in a fluid sample.

FIG. 2A is a flowchart 200 illustrating operation of an example method of determining a white blood cell concentration in a fluid sample. Reference is made to the system 100 in FIG. 1 for an example system for performing the method.

The method in flowchart 200 may begin with the insertion of the vial 110 (in FIG. 1) at step 202. The vial 110 may be detected, for example, using a spring-loaded switch in the vial receptacle 104 (in FIG. 1) that may be opened by the insertion of the vial 110. Upon detection of the vial, and/or press of a button, the device 102 may power up, or perform an initialization of the device 102. During the initialization process, the WBC light source (e.g. the LED) may be turned on as shown at step 204. When the device is ready, the electrical signals at the WBC optical sensor may be input at step 206 for a time period, T, which may be between 10 and 120 seconds in an example implementation. After expiration of time, T, the power to the LED may be turned off at step 208. In an example implementation, the WBC electrical signal may be communicated unprocessed to the sensor data processor 182 for analysis. In another implementation, the WBC electrical signal may be processed at step 210 to determine an average—or other statistical parameters—prior to communication to the sensor data processor 182.

At the sensor data processor 182, the WBC electrical signal may be input into an algorithm or lookup table in which electrical signals may be paired with WBC concentrations. An example for obtaining and using a WBC concentration calibration curve is described in detail below. The calibration curve may be used to identify a WBC concentration corresponding to the WBC electrical signal at step 212. At step 214, the WBC concentration may be displayed on the display 170 on the device 102. The WBC concentration may also be stored in the patients EHR at step 216.

Figure 2B:
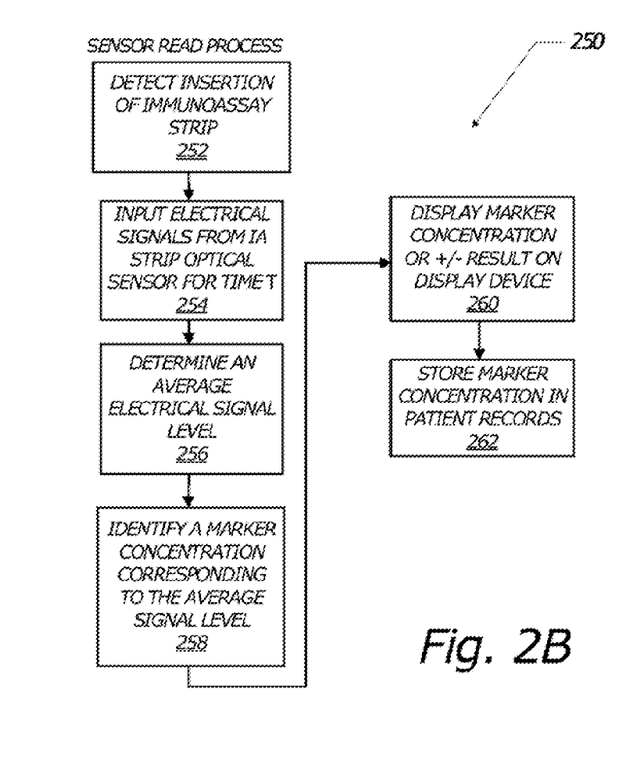
FIG. 2B is a flowchart illustrating operation of an example method of determining a concentration for a marker in a patient's fluid sample used to determine if the patient has a periprosthetic joint infection (PJI).

FIG. 2B is a flowchart 250 illustrating operation of an example method of determining a concentration for a marker in a patient's fluid sample used to determine if the patient has a periprosthetic joint infection (PJI). It is noted that the method 250 in FIG. 2B may be performed for the LE immunoassay strip or for the CRP immunoassay strip, or for any other immunoassay strip configured for another analyte. The method 250 in FIG. 2B may be initiated upon detection of the insertion of an immunoassay strip or press of a button at step 252. The detection of the insertion of the immunoassay strip may be performed by a switch as described for the vial receptacle, or optically using the immunoassay optical sensor, or some other optical sensor implemented for that purpose. At step 254, the electrical signal generated by the immunoassay optical sensor may be received for a period of time, T, which may be between 1 and 5 minutes in an example implementation. At step 256, the immunoassay electrical signals may be analyzed to determine an average or characteristic changes over time. Other statistics may be computed as well. Alternatively, steps 256-258 may be performed after the immunoassay electrical signals may be communicated to the sensor data processor 182. At step 258, a marker concentration corresponding to the immunoassay electrical signal may be identified. The identification of the marker concentration may be performed using an algorithm similar to the process used for the WBC concentration, or threshold(s) corresponding to a range of qualitative results. At step 260, the marker concentration may be displayed on the display 170. Alternatively, at step 260, a plus or minus result may be displayed to indicate whether the sample is positive or negative for an infection. At step 262, the marker concentration may be stored in the patient records in the database 184.

The method 250 may be performed, for example, in obtaining the LE concentration and the CRP concentration. Other markers for which immunoassay strips may be provided, such as alpha-defensin, may be analyzed using a similar process.

Figure 3:
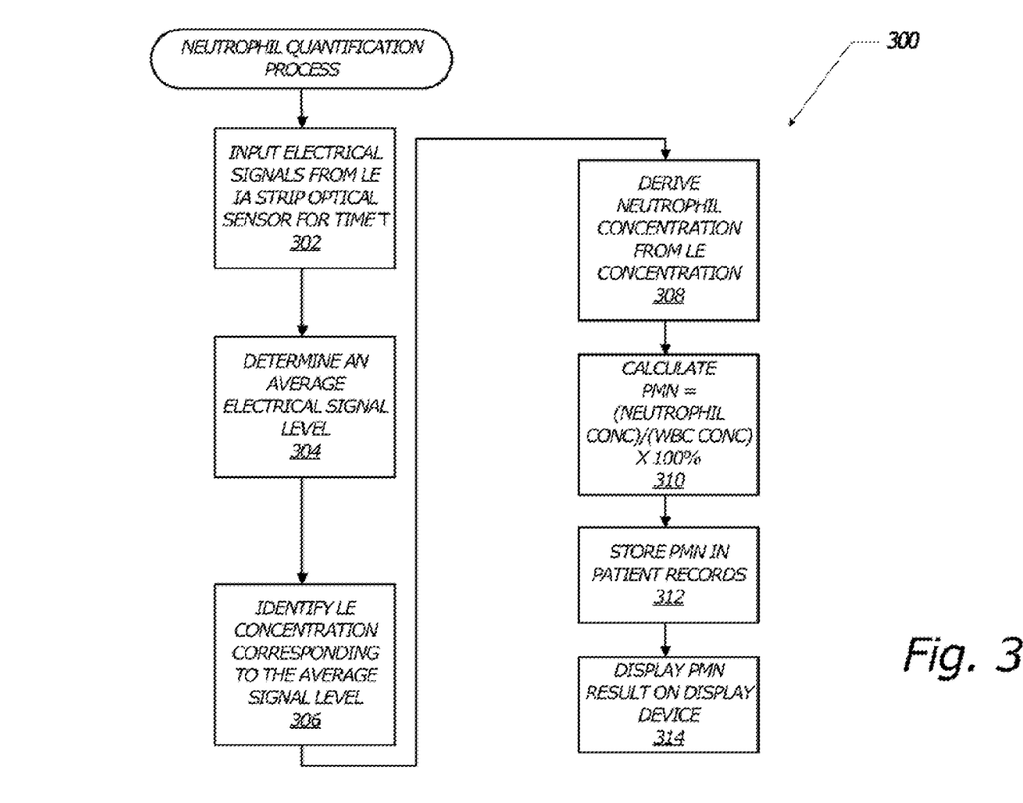
FIG. 3 is a flowchart illustrating operation of an example method of determining a percentage of neutrophils in a patient's fluid sample to determine if the patient has a PJI.

The methods illustrated by flowcharts 200 and 250 in FIGS. 2A and 2B provide a physician with measurements of the WBC concentration and the results of immunoassays of selected PJI markers such as the LE concentration, the CRP concentration, or both. Where the measurements include the LE concentration, the sensor data processor 182 may provide a PMN percentage. FIG. 3 is a flowchart illustrating operation of an example method of determining a percentage of neutrophils (PMN) in a patient's fluid sample. The LE concentration provides a measure that correlates with the number of leukocytes in the fluid sample that may be of the specific type for fighting infections. The more leukocytes in the fluid sample that may be of the bacteria fighting type, the more likely a PJI is indicated. The percentage of white blood cells that may be of the specific type for fighting infections may be indirectly calculated to a useful degree of accuracy by dividing a neutrophil concentration—derived algorithmically from the measured LE concentration—by the WBC concentration.

To determine the PMN percentage, an example implementation of the device determines a LE concentration. The LE concentration may be determined using the method 250 in FIG. 2B where the marker is leukocyte esterase. The method steps 252-258 are shown in FIG. 3 indicating the marker is LE. The method steps are described here with reference to FIG. 3 for clarity.

The method 300 may be initiated upon detection of the insertion of a LE immunoassay strip. At step 302, the electrical signals generated by the LE immunoassay optical sensor may be received for a period of time, T, which may be between 1 and 5 minutes in an example implementation. At step 304, the immunoassay electrical signals may be analyzed to determine an average. Other statistics may be computed as well. Alternatively, steps 304-312 may be performed after the immunoassay electrical signals may be communicated to the sensor data processor 182. At step 306, a LE concentration corresponding to the immunoassay electrical signal may be identified. The identification of the LE concentration may be performed using a calibration curve similar to the process used for the WBC concentration. At step 308, a neutrophil concentration may be correlated from the LE concentration. At step 310, the PMN percentage may be calculated as a percentage of neutrophil concentration in the WBC concentration. The PMN percentage may then be stored in the patient's records at step 312. The PMN percentage may also be displayed on the display 170 of the sensor reader device at step 314.

Figure 4:
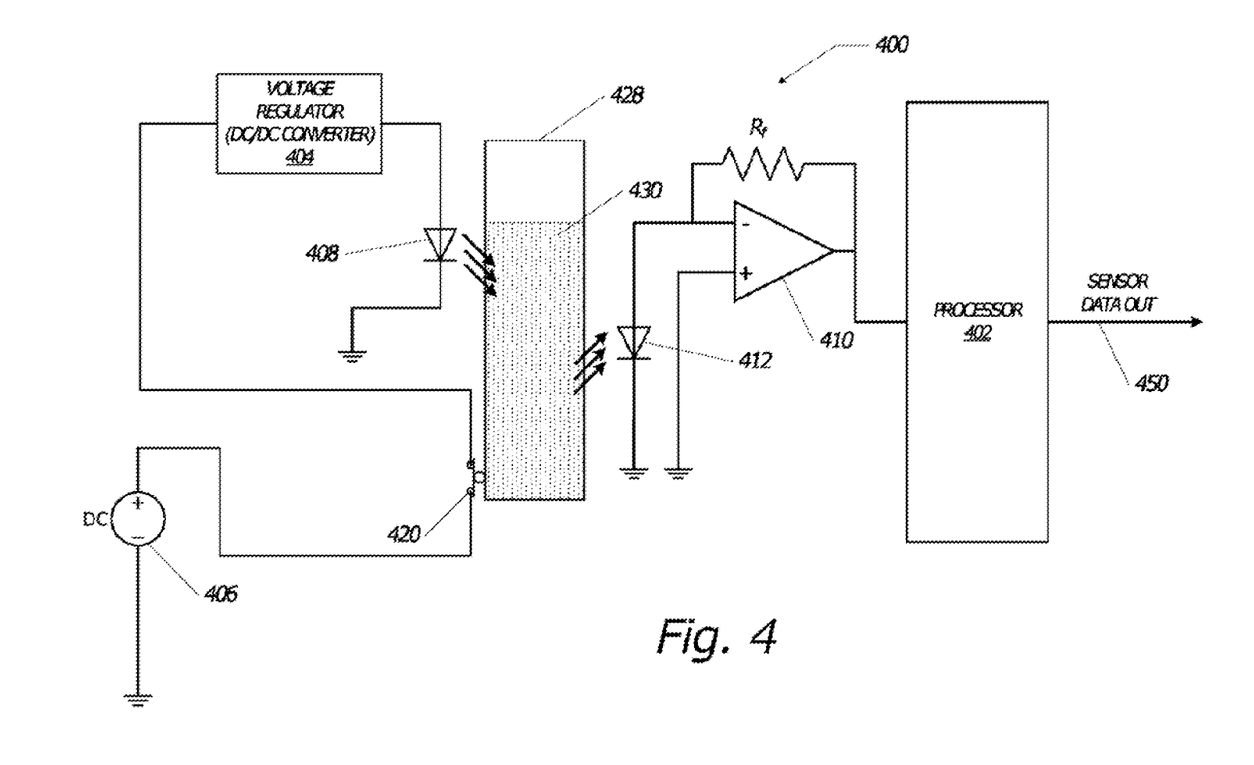
FIG. 4 is an example implementation of a circuit for determining a white blood cell concentration in a fluid sample.

FIG. 4 is an example implementation of a circuit 400 for determining a white blood cell concentration in a fluid sample 430. The example circuit 400 in FIG. 4 includes a processor 402, a voltage regulator 404, a power source 406, an LED 408, a transimpedance amplifier 410, a photodiode 412, and a switch 420. The circuit 400 may be modified to operate as a circuit for determining a marker concentration in conjunction with an immunoassay for another marker. The modification may include replacement of the LED 408 with one or more LEDs sensitive to relevant wavelengths and the selection of a photodiode 412 that may be sensitive to an immunoassay for a different marker.

The circuit 400 in FIG. 4 may be activated by insertion of a vial 428 in the vial receptacle 104 (in FIG. 1). The insertion of the vial 428 pushes the switch 420 to the closed position connecting the battery 406 to the voltage regulator 404. The voltage regulator provides a current source using a DC/DC or AC/DC converter to supply a current to the LED 408. The switch 420 may be configured to power other components in the sensor reader device such as, for example, the processor 402, or the sensor reader device itself.

The processor 402 may initialize the system for a reading of the photodiode 412. The reading of the photodiode 412 involves inputting a voltage level generated by the photodiode 412 that may be indicative of the intensity of light received by the photodiode 412. The LED 408 may be selected to emit a light at a selected wavelength and the photodiode 412 may be selected for its sensitivity to the selected wavelength. In one an example implementation, the LED 412 may be an LED that emits light at a wavelength of 587 nm and the photodiode may be selected for sensitivity to a wavelength range of about 580-595 nm.

The voltage generated by the photodiode 412 in FIG. 4 is amplified by the amplifier 410. In one example implementation, the amplifier 410 may be an ultra-low bias current junction field-effect transistor (JFET), which may be connected to the processor 402 and use a feedback resistor $R_f$. This amplifier may be included in an analog front-end (AFE) chip. The voltage generated by the photodiode 412 may be input to the processor 402 for a period of time, T. In an example implementation, the processor 402 may input the voltage for a period of between about 10 to 120 seconds. The input to the processor 402 may connect the voltage to an analog-to-digital converter (ADC), which digitizes the analog voltage level for processing. The processor 402 may convert the voltage levels to a stream of digital values for communication to the hub 180 (in FIG. 1). The processor 402 may also be configured to perform digital signal processing functions such as filtering, reducing the data, or performing statistical functions. The processor 402 processes the stream of voltage levels and outputs the stream as digital sensor data at 450.

III. Examples: WBC Concentration Calibration Curve

Referring to FIG. 4, the photodiode 412 generates voltage levels corresponding to the light intensity sensed in the wavelength range to which the photodiode 412 is sensitive. The voltage levels may be correlated with the concentration of white blood cells in the fluid sample. For a specific sensor-analyte combination, a calibration curve may be created and stored for use in subsequent tests. The calibration curve may be stored as a formula, or as a table in which voltage levels may be paired with corresponding concentrations. The following describes a method for calibrating a white blood cell function in an example implementation of a sensor reader device.

A. Testing Procedure

A testing procedure was performed on a prototype version of the in vitro diagnostic sensor reader device. The prototype device was constructed from off-the-shelf electronics components connected via bread- and breakout boards where applicable. The prototype sensor reader device was positioned around a polyethylene terephthalate (PET) sample tube such that the LED and photodiode were disposed at a relative 135° angle. The sample tube was filled with serially diluted solutions of white blood cells in synovial fluid. For each of these test samples, 10 seconds of voltage data was recorded from the output of the photodiode amplifier. The sensor data was analyzed to assess the optical sensor's precision and accuracy when measuring the white blood cell concentration in synovial fluid.

B. Standard Curve Creation

Figure 5:
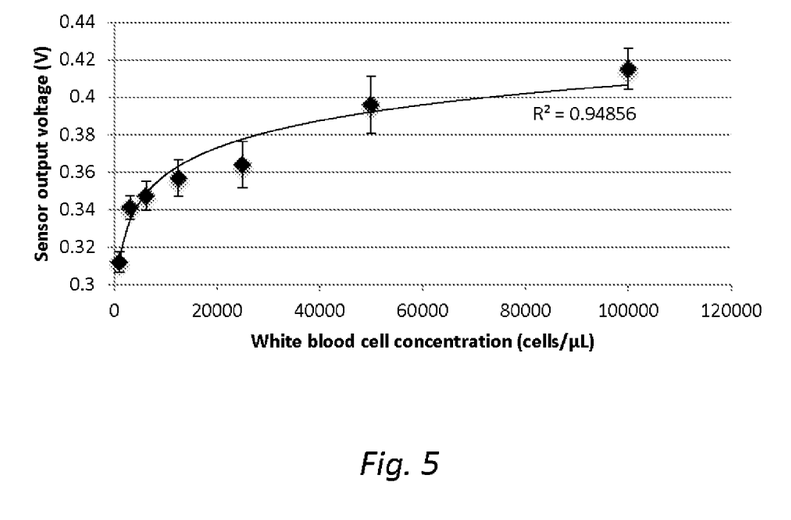
FIG. 5 shows a standard curve of sensor output voltage versus white blood cell concentration.
Figure 6:
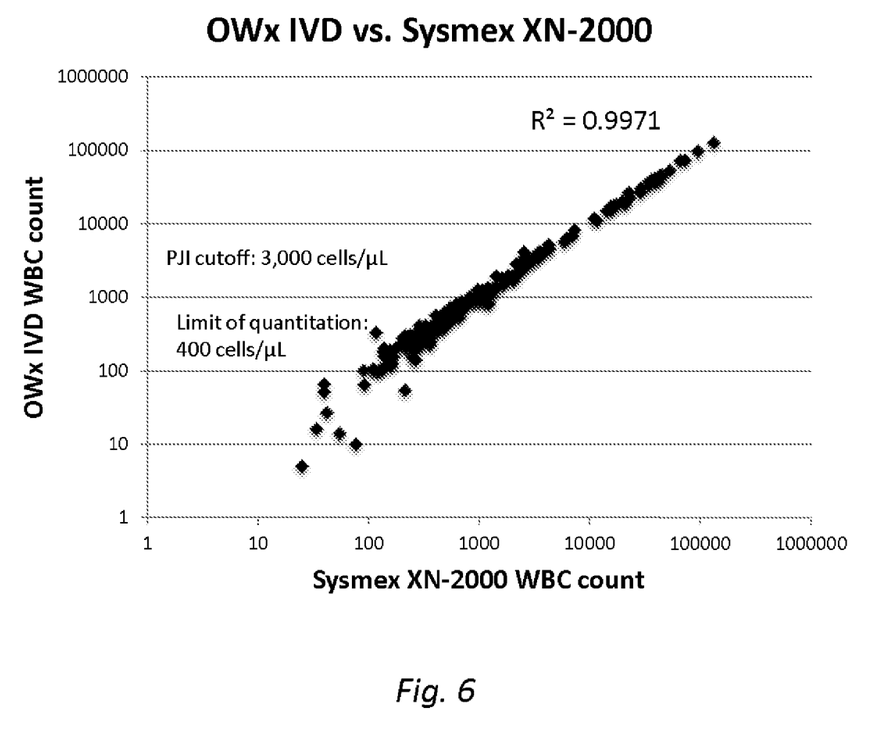
FIG. 6 shows results of IVD device WBC sensor validation testing.

For the first 10 sample batches, the mean voltages of each filtered sample were plotted to create a standard curve of sensor output voltage against WBC concentration (see FIG. 5). The data used to construct the standard curve was analyzed for initial precision, i.e. correlation, to serve as the baseline for accuracy and precision analysis of further sample tests. The data from the remaining 10 sample batches were analyzed against the standard curves to determine the accuracy and precision of those measurements. The standard curve was used to create an algorithm that was then tested on 192 clinical synovial fluid samples, producing the results shown in FIG. 6.

C. Data Analysis

The sensor used in the prototype device has been adjusted for improved resolution at threshold cellular concentrations, meaning that the results computed from its output may have a lower margin of error at those lower concentrations. Table 1 below shows the initial precision of the sensor demonstrated in the first round of testing at each cellular concentration. Where the precision is either under 500 cells/µL or within 10% of the actual value

TABLE 1

White blood cell concentration sensor output precision

| | Cells/µL | | | | | | |
|---|---|---|---|---|---|---|---|
| | 1,000 | 3,125 | 6,250 | 12,500 | 25,000 | 50,000 | 100,000 |
| Precision | 293 | 491 | 401 | 509 | 1,376 | 3,438 | 5,865 |
| % error | 29.3% | 15.7% | 6.4% | 4.1% | 5.5% | 6.9% | 5.9% |

TABLE 1-continued

White blood cell concentration sensor output precision

| Cells/μL | | | | | | |
|---|---|---|---|---|---|---|
| 1,000 | 3,125 | 6,250 | 12,500 | 25,000 | 50,000 | 100,000 |

| Acceptable? | Yes | Yes | Yes | Yes | Yes | Yes | Yes |

More generally, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A system for detecting an infection in a fluid sample drawn from a patient at the patient's point-of-care, the system comprising:
   a white blood cell (WBC) concentrator, the WBC concentrator comprising:
   i. a vial receptacle sized to receive a vial containing the fluid sample;
   ii. one or more light sources operable to illuminate the fluid sample in the vial; and
   iii. a vial optical sensor oriented to detect scattered light intensity, absorbed light intensity, or both by white blood cells in the fluid sample, wherein the vial optical sensor is configured to convert the light intensity to a vial electrical signal;
   at least one immunoassay (IA) strip reader comprising:
   i. at least one IA strip receptacle sized to receive an IA strip having an analyte reagent and a portion of the fluid sample, wherein the analyte reagent is configured to generate an analyte light intensity from a reaction between the analyte reagent and an analyte in the fluid sample; and
   ii. an IA strip optical sensor oriented to detect the analyte light intensity, wherein the IA strip optical sensor is configured to convert the analyte light intensity to an IA analyte electrical signal; and
   an optical sensor reader, the optical sensor reader comprising a processor configured to receive the vial electrical signals and the IA analyte electrical signals, to store the vial electrical signals as vial sensor data and the IA analyte electrical signals as IA analyte sensor data, and to communicate the vial sensor data and the IA analyte sensor data over a communications interface, the processor in communication with the communications interface configured to determine a WBC concentration from the vial sensor data and a leukocyte concentration and from the IA analyte sensor data.

2. The system of claim 1, wherein the analyte is leukocyte esterase (LE), the analyte reagent is an LE reagent, and the IA strip optical sensor is an LE optical sensor configured to detect the analyte light intensity at a wavelength range between about 425 nanometers (nm) and about 475 nm.

3. The system of claim 1, further comprising:
   a c-reactive protein (CRP) immunoassay strip receptacle sized to receive a CRP immunoassay strip, the CRP immunoassay strip having a portion of the fluid sample and a CRP reagent, the CRP reagent configured to react with CRP in the portion of the fluid sample.

4. The system of claim 3, further comprising:
   a CRP optical sensor oriented to detect light generated by the reaction of CRP with the CRP reagent.

5. The system of claim 1, further comprising:
   a quality control optical sensor oriented to detect light generated by the IA strip, wherein wavelength to detect the analyte light intensity ranging between 600-630 nanometers (nm) corresponding to a detected wavelength for light reflected by hemoglobin in the fluid sample.

6. The system of claim 1, wherein the analyte is alpha-defensin, the analyte reagent is an alpha-defensin reagent, and the IA strip optical sensor is an alpha-defensin optical sensor configured to detect the analyte light intensity at a wavelength range between about 400 nm and about 700 nm.

7. A system for detecting an infection in synovial fluid drawn from a patient, the system comprising:
   a vial receptacle sized to receive a vial containing the fluid sample;
   a light source disposed in the vial receptacle and operable to illuminate the fluid sample in the vial;
   a vial optical sensor disposed in the vial receptacle and operable to detect light scattered by white blood cells in the fluid sample and to generate a vial electrical signal indicative of an intensity of the light detected;
   at least one immunoassay strip receptacle sized to receive a corresponding at least one immunoassay strip, wherein each at least one immunoassay strip includes a reagent configured to react with a corresponding at least one analyte substance and to generate light substantially within a wavelength range corresponding to the analyte substance when the immunoassay strip is in contact with the fluid sample;
   at least one optical sensor associated with the at least one immunoassay strip receptacle and different than the vial optical sensor, the at least one optical sensor corresponding to the at least one analyte substance and oriented to detect light within the wavelength range corresponding to the one of the at least one analyte substance when the at least one immunoassay strip is inserted into the at least one immunoassay strip receptacle, wherein the at least one optical sensor is configured to generate an immunoassay electrical signal indicative of an intensity of light detected within the wavelength range corresponding to the one of the at least one analyte substance; and
   a processor configured to receive the vial electrical signal and the immunoassay electrical signal as sensor data and to communicate the sensor data to a communications interface, wherein the processor in communication with the communications interface is configured to diagnose a presence or absence of a periprosthetic joint infection in the fluid sample based on the sensor data.

8. The system of claim 7, wherein the at least one analyte substance includes leukocyte esterase (LE) and c-reactive protein (CRP), and the at least one immunoassay strip receptacle includes:

an LE immunoassay strip receptacle sized to receive an LE immunoassay strip having an LE reagent configured to react with LE; and a CRP immunoassay strip receptacle sized to receive a CRP immunoassay strip having a CRP reagent configured to react with CRP.

9. The system of claim 8, wherein the at least one optical sensor includes:

an LE optical sensor oriented to detect light generated by the reaction of the LE with the LE reagent, wherein the detected light being within a wavelength range of 425-475 nanometers (nm).

10. The system of claim 8, wherein the at least one optical sensor includes:

a CRP optical sensor oriented to detect light generated by the reaction of CRP with the CRP reagent.

11. The system of claim 8, wherein the at least one optical sensor includes:

a quality control optical sensor oriented to detect light generated by the LE immunoassay strip ranging from 600-630 nanometers (nm) corresponding to a detected wavelength for light reflected by hemoglobin in the fluid sample.

12. A method for evaluating analytes for periprosthetic joint infection (PJI) in a synovial fluid sample, the method comprising:

providing a vial receptacle sized to receive a vial containing a fluid sample;

providing one or more light sources oriented to illuminate the fluid sample in the vial;

providing a vial optical sensor oriented to detect light scattered, light absorbed, or both by white blood cells in the fluid sample, wherein the vial optical sensor is configured to generate a vial electrical signal indicative of an intensity of detected light;

providing at least one immunoassay strip receptacle sized to receive a leukocyte esterase (LE) immunoassay strip having an LE analyte reagent and a portion of the fluid sample, wherein the LE analyte reagent is configured to generate an analyte light intensity from a reaction between the LE analyte reagent and an analyte in the fluid sample;

providing an immunoassay optical sensor oriented to detect the analyte light intensity and to convert the analyte light intensity to an LE immunoassay analyte electrical signal; and providing a processor communicatively coupled to the vial optical sensor and the immunoassay strip optical sensor via a communications interface, the processor configured to (i) receive an indication of a presence of the vial containing fluid sample in a vial receptacle, (ii) provide an instruction to apply to the one or more light sources directed at the vial containing the fluid sample, (iii) provide an instruction to initiate the vial optical sensor (iv) receive the vial electrical signal from the vial optical sensor indicative of the intensity of detected light, (v) receive an indication of a presence of the LE immunoassay strip in the at least one immunoassay receptacle, (vi) provide an instruction to initiate the immunoassay optical sensor, (vii) receive LE immunoassay analyte electrical signal from the immunoassay optical sensor, and (viii) calculate a white blood cell (WBC) concentration and a leukocyte concentration from the vial electrical signal and the LE immunoassay analyte electrical signal.

13. The method of claim 12, wherein the LE immunoassay analyte electrical signal comprises an electrical signal indicative of light at a wavelength range of 425-475 nanometers (nm) as a ratio to the amount of detected light at a wavelength range of 500-550 nm.

14. The method of claim 12, further comprising:

providing a c-reactive protein (CRP) immunoassay (IA) strip in a CRP IA receptacle, wherein the CRP IA strip includes a CRP reagent and a portion of the fluid sample, wherein the CRP reagent is configured to generate a second analyte light intensity from a second reaction between the CRP reagent and a second analyte in the fluid sample; and providing a CRP optical sensor oriented to detect the second analyte light intensity and to convert the second analyte light intensity to a CRP IA analyte electrical signal, wherein the processor, operably coupled to the CRP optical sensor via the communications interface, is configured to (i) receive an indication of a presence of the CRP IA strip in the CRP IA receptacle, (ii) provide an instruction to initiate the CRP optical sensor, (iii) receive the CRP IA analyte electrical signal, and (iv) calculate a CRP concentration from the CRP IA analyte electrical signal.

15. The method of claim 12, further comprising:

providing a hemoglobin (Hb) immunoassay (IA) strip in an Hb IA receptacle, wherein the Hb IA strip includes an Hb reagent and a portion of the fluid sample, wherein the Hb reagent is configured to generate a third analyte light intensity from a third reaction between the Hb reagent and a third analyte in the fluid sample; and providing an Hb optical sensor oriented to detect the third analyte light intensity and to convert the third analyte light intensity to an Hb IA analyte electrical signal wherein the processor, operably coupled to the Hb optical sensor via the communications interface, is configured to (i) provide an instruction to initiate the Hb optical sensor, (ii) receive the Hb analyte electrical signal, and (iii) calculate an Hb concentration from the Hb IA analyte electrical signal.

16. The method of claim 12, wherein the LE immunoassay analyte electrical signal comprises an electrical signal indicative of light at a wavelength range of 600-630 nm.

17. The method of 12, wherein the processor is further configured to determine a neutrophil percentage (PMN) based on the leukocyte concentration divided by the WBC concentration.

18. A system for measuring analytes for an infection in synovial fluid drawn from a patient, the system comprising:

a vial receptacle sized to receive a vial containing a fluid sample;

a light source disposed in the vial receptacle to illuminate the fluid sample in the vial;

a vial optical sensor disposed in the vial receptacle to detect light scattered by white blood cells in the fluid sample and to generate a vial electrical signal indicative of an intensity of the light detected;

a first immunoassay strip receptacle sized to receive a first immunoassay strip having a first reagent configured to react with a first substance as a analyte for a periprosthetic infection and to generate light substantially within a first wavelength range when the first immunoassay strip is in contact with the fluid sample;

a first optical sensor configured to detect light in the first wavelength range when the first immunoassay strip is inserted into the first immunoassay strip receptacle and to generate a first immunoassay electrical signal indicative of the intensity of light detected within the first wavelength range;

a second immunoassay strip receptacle for holding a second immunoassay strip having a second reagent configured to react with a second substance as a second analyte for a periprosthetic infection and to generate light substantially within a second wavelength range when the second immunoassay strip is in contact with the fluid sample;

a second optical sensor configured to detect light in the second wavelength range when the second immunoassay strip is inserted into the second immunoassay strip receptacle and to generate a second immunoassay electrical signal indicative of the intensity of light detected within the second wavelength range; and a processor configured to receive the vial electrical signal, the first immunoassay electrical signal, and the second immunoassay electrical signal as sensor data, and to communicate the sensor data to a communications interface, wherein the processor in communication with the communications interface is configured to analyze the sensor data and diagnose the presence or absence of a periprosthetic joint infection in the fluid sample based on the sensor data.

19. The system of claim 1, further comprising a display operably connected to the processor, the display operable to display the WBC concentration and the leukocyte concentration.

20. The system of claim 7, further comprising a display operably connected to the processor, the display operable to display information indicative of the presence or absence of a periprosthetic joint infection in the fluid sample.

21. The method of claim 12, further comprising a display, operably connected to the processor, for displaying the WBC concentration and the leukocyte concentration.

* * * * *